(12) United States Patent
Belitz

(10) Patent No.: US 9,089,201 B1
(45) Date of Patent: Jul. 28, 2015

(54) TOOTHBRUSH CLEANING DEVICE AND METHOD WITH WATER JETS

(71) Applicant: Adam Belitz, Monroe Township, NJ (US)

(72) Inventor: Adam Belitz, Monroe Township, NJ (US)

(*) Notice: Subject to any disclaimer, the term of this patent is extended or adjusted under 35 U.S.C. 154(b) by 0 days.

(21) Appl. No.: 14/661,096

(22) Filed: Mar. 18, 2015

(51) Int. Cl.
*A46B 17/06* (2006.01)
*B08B 3/02* (2006.01)
*A61C 19/00* (2006.01)

(52) U.S. Cl.
CPC .............. *A46B 17/06* (2013.01); *A61C 19/002* (2013.01); *B08B 3/02* (2013.01)

(58) Field of Classification Search
None
See application file for complete search history.

(56) References Cited

U.S. PATENT DOCUMENTS

| | | | |
|---|---|---|---|
| 3,189,490 A | 6/1965 | Scott | |
| 3,499,792 A | 3/1970 | Veith | |
| 3,869,746 A | 3/1975 | Man-King | |
| 4,389,016 A | 6/1983 | Gibbs | |
| 4,509,545 A | 4/1985 | Trotter | |
| 4,606,777 A | 8/1986 | Brow | |
| 4,995,749 A | 2/1991 | Gornik | |
| 5,193,446 A | 3/1993 | Olusczak et al. | |
| 5,381,959 A | 1/1995 | Malkin | |
| 5,876,135 A * | 3/1999 | Wang et al. | 401/46 |
| 5,961,046 A | 10/1999 | Joubran | |
| 6,463,943 B1 | 10/2002 | Monroe | |
| 7,216,663 B2 | 5/2007 | Vu | |
| 7,322,535 B2 | 1/2008 | Erdely | |
| 2011/0000506 A1 | 1/2011 | Martin | |
| 2013/0165828 A1 | 6/2013 | Sullivan | |

* cited by examiner

*Primary Examiner* — Michael Kornakov
*Assistant Examiner* — Ryan Coleman
(74) *Attorney, Agent, or Firm* — Michael J. Feigin, Esq.; Feigin & Associates, LLC

(57) ABSTRACT

A device for cleaning a toothbrush, attachable to a faucet expelling water in a first direction, the device including: an adapter mountable on a water expelling end of the faucet; and a cylindrical cleaning element in fluid flow communication with the adapter and disposed, when the adapter is mounted on the faucet, in a direction transverse to the first direction, the cylindrical cleaning element including a cylindrical housing and a water expelling cylindrical element, disposed within the cylindrical housing and including multiple rows of circumferentially disposed nozzles for expelling water jets, the water expelling cylindrical element defining an interior space accessible via circular portal at an end thereof, wherein when water is expelled from the faucet, at least some water is directed in the transverse direction and expelled through the nozzles in the water expelling cylindrical element.

9 Claims, 6 Drawing Sheets

TOOTHBRUSH CLEANING DEVICE AND METHOD WITH WATER JETS

FIELD OF THE DISCLOSED TECHNOLOGY

The disclosed technology relates generally to oral health and hygiene and, more specifically, to a water velocity increasing device for cleaning and/or disinfecting a toothbrush, which can be connected by an adapter to a standard faucet.

BACKGROUND OF THE DISCLOSED TECHNOLOGY

Many people, and particularly children, struggle to get their toothbrush properly clean. The toothpaste, as well as plaque and bacteria removed from the mouth by the process of tooth-brushing, tend to get caught between the bristles of the toothbrush. As such, proper cleaning of the toothbrush requires application of some force to the bristles. Typically, users tend to rub the bristles of the toothbrush with their finger while the toothbrush is under running water. However, this type of action is often counterproductive, as it may push the toothpaste and/or unwanted particles further in between the bristles, and may transfer the undesired particles and bacteria onto, or from, the user's hands or fingers, from whence they may be spread around things the user touches.

The prior art describes various types of cleaning devices for cleaning brushes of different kinds, without requiring the user's hands to engage the brush.

U.S. Pat. No. 4,995,749 to Gornik discloses a paint roller cleaner with a hollow annular member and nozzle elements projecting into the annular member. For use, the user pushes a paint roller though the annular member to clean the roller. The annular member is functionally connected to an adapter which attaches to a faucet directing water transfer to the adapter. However, this reference does not appear to teach the expelling of water downwards from the faucet when the adapter is attached thereto, or using the adapter and annular member to clean a toothbrush.

US Patent Application Publication No. 2011/0000506 to Martin discloses a filter cleaner with a spray device in a tubular stem slidably disposed within a sleeve. Nozzles are arranged within an interior member of the spray device. However, this reference does not appear to teach selecting to expel water downwards from the faucet when the adapter is attached thereto, or using the adapter and annular member to clean a toothbrush.

US Patent Application Publication No. 2013/0165828 to Sullivan discloses a faucet adapter cleaning device. The device selectively allows one to transversely direct water from a faucet to a second device for cleaning teeth. However, this reference does not appear to teach using circular jets of water from nozzles or using the adapter to clean a toothbrush.

Therefore, there exists a need in the art for a device and method for cleaning a toothbrush, which would be connectable to a faucet and enable expelling of water downward from the faucet, and would selectively provide pressurized water jets from circumferentially disposed nozzles, strong enough to remove the unwanted particles from the toothbrush without requiring the user's fingers to engage the bristles.

SUMMARY OF THE DISCLOSED TECHNOLOGY

The disclosed technology relates generally to oral health and hygiene and, more specifically, to a water jet powered device for cleaning and/or sterilizing a toothbrush, which may be connected by an adapter to a standard faucet.

According to an aspect of some embodiments of the teachings herein, there is provided a device for cleaning a toothbrush, attachable to a faucet expelling water in a first direction, the device including: an adapter mountable on a water expelling end of the faucet; and a cylindrical cleaning element in fluid flow communication with the adapter and disposed, when the adapter is mounted on the faucet, in a direction transverse to the first direction, the cylindrical cleaning element including a cylindrical housing and a water expelling cylindrical element, disposed within the cylindrical housing and including multiple rows of circumferentially disposed nozzles for expelling water jets, the water expelling cylindrical element defining an interior space accessible via circular portal at an end thereof, wherein when water is expelled from the faucet, at least some water is directed in the transverse direction and expelled through the nozzles in the water expelling cylindrical element.

In some embodiments, the cylindrical cleaning element is configured to have a toothbrush moved longitudinally back and forth therein, such that water jets expelled from the nozzles cleans bristles of the toothbrush. The "nozzles" is any hole or portal through which water passes from within the body of the cylinder to an internal cavity within the cylinder.

In some embodiments, the device further includes a valve functionally associated with the adapter, the valve having a water-flow position allowing water to be expelled from the faucet in the first direction and a cleaning position in which all water flowing into the faucet is directed in the transverse direction and is expelled through the nozzles.

In some embodiments, the device further includes a Venturi fitting in fluid flow communication with a disinfectant or bacterial rinse receptacle, the Venturi fitting mounted onto a supply line into the faucet, such that when the valve is in the cleaning position, detergent is drawn from the detergent receptacle into water in the supply line and is expelled with the water from the supply line through the nozzles.

In some embodiments, the cylindrical cleaning element further includes a port allowing water to leave the interior space of the cylindrical cleaning element, the port being opened based on a change of pressure in the device. In some such embodiments, the pressure change is a result of turning off the faucet. In some such embodiments, the pressure change is a result of moving the valve from the cleaning position to the water flow position. In some embodiments, the port is spring loaded.

In some embodiments, the cylindrical cleaning element further includes a removable decorative outer sleeve disposed about the cylindrical housing. In some such embodiments, the removable decorative outer sleeve has printed thereon at least one of childish images and statements encouraging brushing teeth and toothbrush cleaning.

According to another aspect of some embodiments of the teachings herein, there is provided a method for cleaning a toothbrush, the method including mounting an adapter on a faucet expelling water in a first direction, the adapter being in fluid flow communication with a cylindrical cleaning element disposed, when the adapter is mounted on the faucet, in a direction transverse to the first direction, the cylindrical cleaning element including multiple rows of circumferentially disposed nozzles for expelling water jets and having an interior space defined therein, activating the faucet such that when water is expelled from the faucet, at least some water is directed in the transverse direction and expelled through the nozzles, and moving a toothbrush to be cleaned longitudinally back and forth within the interior space such that the water jets impinge on bristles of the toothbrush for cleaning thereof.

In some embodiments, mounting an adapter includes mounting an adapter having a valve functionally associated therewith, the valve having a water-flow position in which water is expelled from the faucet in the first direction and a cleaning position in which all water flowing into the faucet is directed in the transverse direction and is expelled through the nozzles, and the method further includes, prior to activating the faucet, moving the valve into the cleaning position.

In some embodiments, the method further includes, prior to activating the faucet, fluidly connecting to a supply line of the faucet, via a Venturi fitting, a detergent receptacle, wherein moving the valve into the cleaning position and activating the faucet decreases pressure in the Venturi fitting such that detergent or bacterial rinse from the receptacle is drawn into the supply line and into nozzles.

In some embodiments, the method further includes, when a pressure changes in the adapter, opening a port in the cylindrical cleaning element and draining remaining water from the interior space of the cylindrical cleaning element. In some embodiments, the method further includes turning off the faucet to cause the pressure changes within the adapter. In some embodiments, the method further includes moving the valve from the cleaning position to the water-flow position to cause the pressure changes within the adapter.

In some embodiments, the method further includes placing a removable decorative outer sleeve about a cylindrical housing of the cylindrical cleaning element. In some such embodiments, placing a removable decorative outer sleeve includes placing a removable decorative outer sleeve which has printed thereon at least one of childish images and statements encouraging brushing teeth and toothbrush cleaning. The sleeve can have an insert which can also be disposable and have an anti-bacterial coating. The insert can be of plastic and replaceable, during each use, or provided with instructions to replace the insert after an interval of time, such as once a month.

DETAILED DESCRIPTION OF EMBODIMENTS OF THE DISCLOSED TECHNOLOGY

In an embodiment of the disclosed technology, a toothbrush cleaning device includes an adapter which is connectable to a faucet, where the faucet expels water in a first direction. The adapter includes a toothbrush cleaning cylinder disposed transversely to the first direction in which the faucet expels water. The cleaning cylinder includes an outer housing potion and an inner cylinder including a plurality of nozzles which, when water is expelled from the faucet into the adapter, expel water jets. A valve forming part of the adapter determines whether water is expelled from the faucet in the first direction, or via the adapter, transversely to the first direction toward the cleaning cylinder.

According to an aspect of some embodiments of the teachings herein, there is provided a device for cleaning a toothbrush, attachable to a faucet expelling water in a first direction, the device including an adapter mountable on a water expelling end of the faucet, and a cylindrical cleaning element in fluid flow communication with the adapter and disposed, when the adapter is mounted on the faucet, in a direction transverse to the first direction, the cylindrical cleaning element including a cylindrical housing and a water expelling cylindrical element, disposed within the cylindrical housing and comprising multiple rows of circumferentially disposed nozzles for expelling water jets, the water expelling cylindrical element defining an interior space accessible via circular portal at an end thereof, wherein when water is expelled from the faucet, at least some water is directed in the transverse direction and expelled through the nozzles in the water expelling cylindrical element.

Embodiments of the disclosed technology will become clearer in view of the following description of the drawings.

Figure 1:
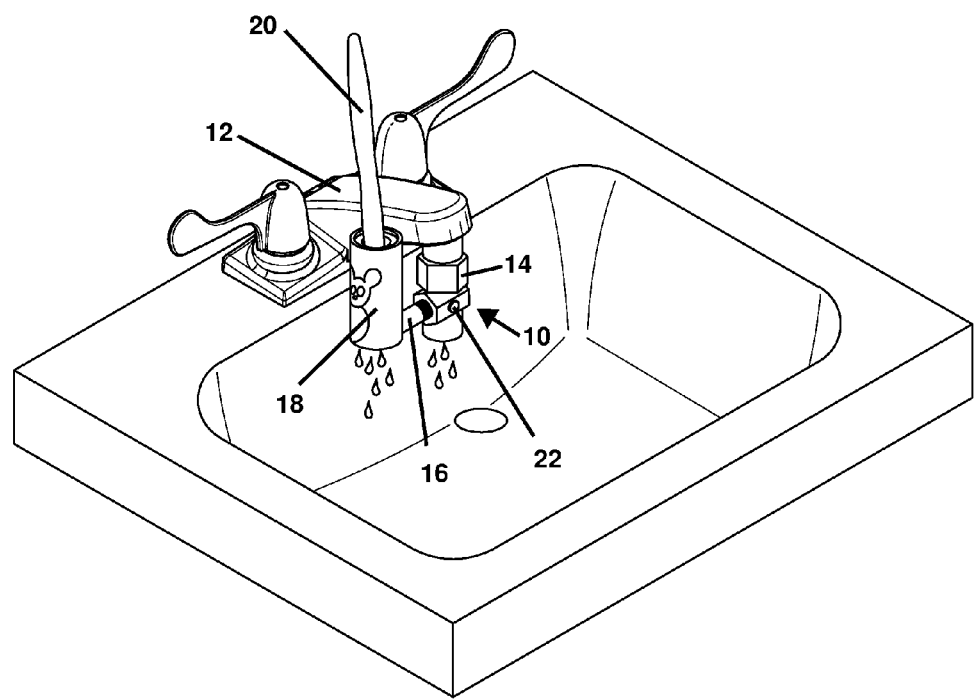
FIG. 1 shows a perspective view of a device for cleaning a toothbrush, according to an embodiment of the disclosed technology, mounted onto a standard faucet.

Reference is now made to FIG. 1 shows a perspective view of a device 10 for cleaning a toothbrush, according to an embodiment of the disclosed technology, mounted onto a standard faucet 12. As seen in FIG. 1, the device 10 includes a faucet adapter 14 which is connectable to faucet 12, which normally expels water in a downward direction. Extending from adapter 14, in a direction transverse to the direction of normal water flow from the faucet, here shown as a horizontal direction, is a pipe 16 terminating in a cylindrical cleaning element 18.

As shown in further detail hereinbelow with reference to FIGS. 2 and 5, cylindrical cleaning element 18 includes nozzles which, when water is directed from faucet 12 through pipe 16 to cylindrical cleaning element 18, expel water jets for cleaning a toothbrush 20 disposed in, or being moved upward and downward within, the interior cavity of cylindrical cleaning element 18.

In some embodiments, when adapter 14 is connected to faucet 12, the water expelled from faucet 12 is split such that some of the water is expelled downward from the faucet, as it would be without the adapter 14, and some of the water is directed through pipe 16 to cylindrical cleaning element 18.

In other embodiments, such as the illustrated embodiment, adapter 14 has a valve, or button 22 associated therewith. Valve or button 22 may be in a water-flow position, in which water is expelled downward from the faucet as would occur if adapter 14 were not connected to the faucet, or may be in a cleaning position, in which all the water flowing through faucet 12 is directed to the cylindrical cleaning element 18 via pipe 16. In the embodiment illustrated in FIG. 1, button 22 is in transition between the water flow position and the cleaning position, such that water is flowing downward from faucet 12 as well as from cylindrical cleaning element 18.

Figure 2:
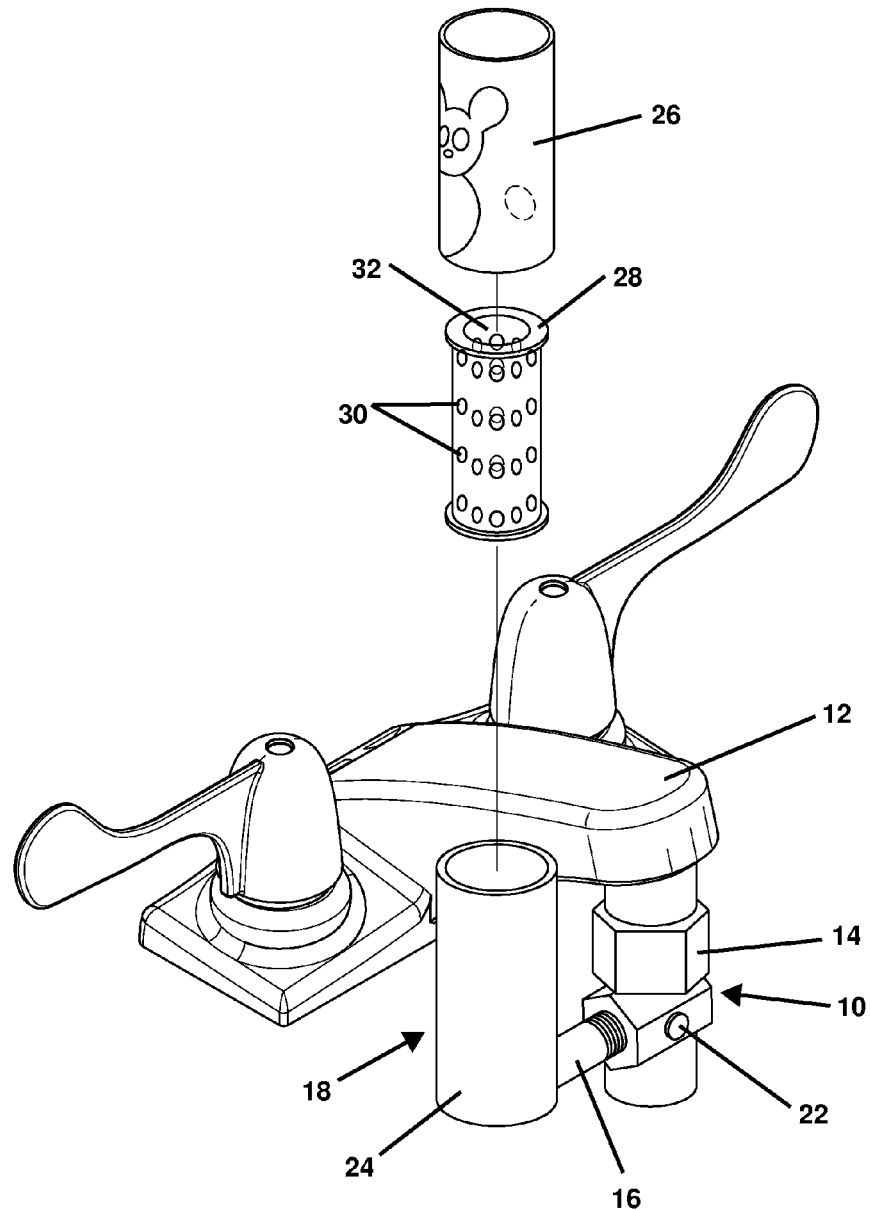
FIG. 2 shows a perspective, partially exploded view of the device for cleaning a toothbrush of FIG. 1, according to an embodiment of the disclosed technology.
Figure 6:
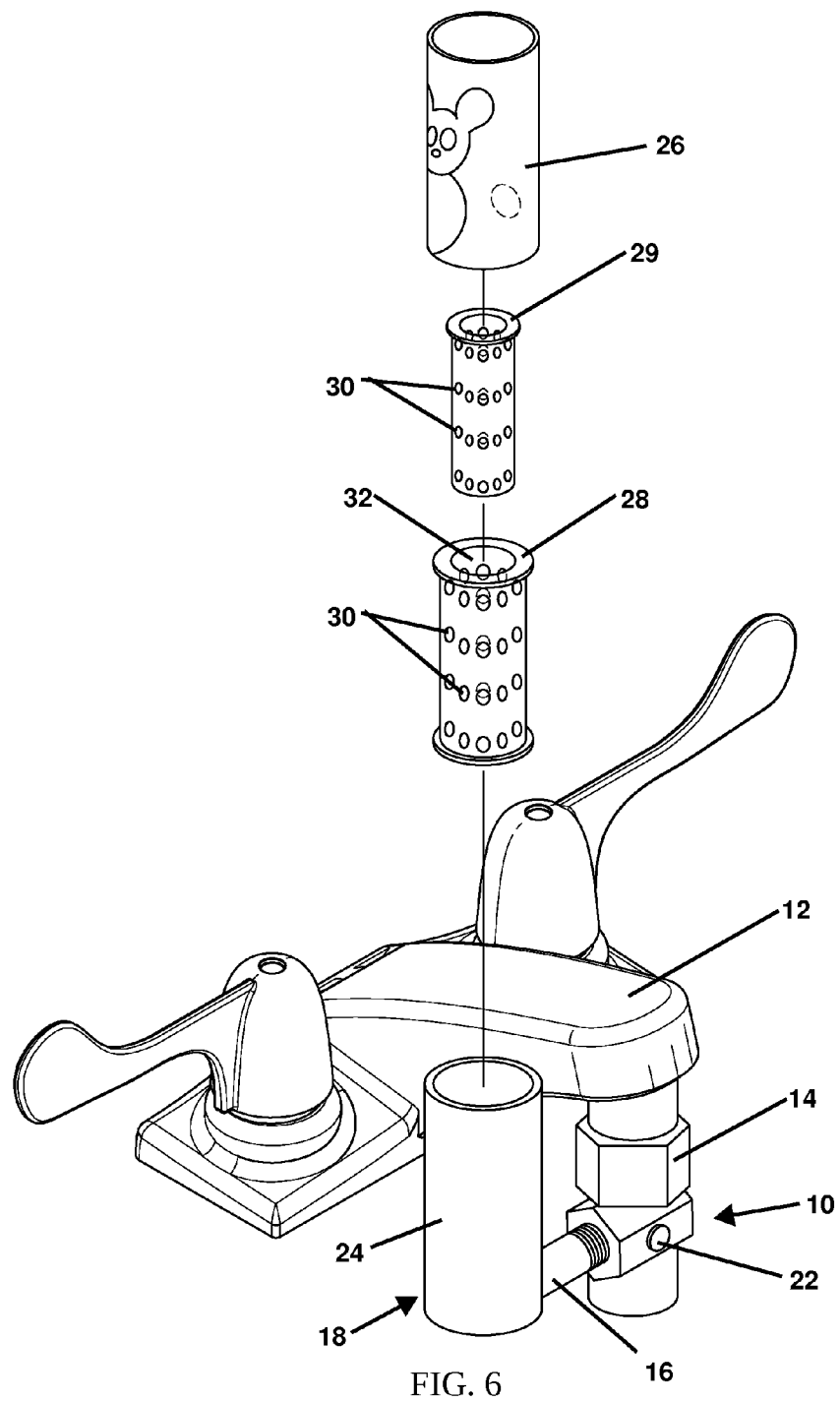
FIG. 6 shows a perspective, partially exploded view of the device for cleaning a toothbrush of FIG. 1, according to another embodiment of the disclosed technology.

Reference is now made to FIGS. 2 and 6, which show perspective, partially exploded views of the device 10 for cleaning a toothbrush, in two embodiments. As seen, cylindrical cleaning element comprises a cylindrical housing 24 connected to pipe 16, the exterior of which may be wrapped with a removable decorative outer sleeve 26. The outer sleeve 26 may be decorated with childish images and/or statements encouraging brushing teeth and toothbrush cleaning, so as to encourage a user, and particularly a juvenile user, to brush their teeth and properly clean their toothbrush. A "childish image" for purposes of this disclosure is a cartoon, animated, or drawn character which is appealing to children.

Disposed within cylindrical housing 24 is a water expelling cylindrical element 28 including multiple rows of circumferentially disposed nozzles 30 for expelling water jets, and defining an interior space 32 accessible via circular portal at an end of the cylinder. The toothbrush to be cleaned is inserted into interior space 32, as explained hereinbelow with reference to FIG. 5. The element 28 can also be disposable, or may include a disposable insert 29 as shown in FIG. 6, which catches grime, toothpaste, and unwanted particles from off the toothbrush when cleaning. This disposable insert can be replaced, or instructions can be provided to replace same, at regular time intervals, such as once a month or after each use or every 10, 20, or 50 uses. As seen in FIG. 6, the disposable insert 29 also includes circumferentially disposed nozzles 30, similar to the nozzles in cylindrical element 28, and includes an interior space 32, which, when the device is constructed, is aligned with the interior space of cylindrical element 28.

Figure 3:
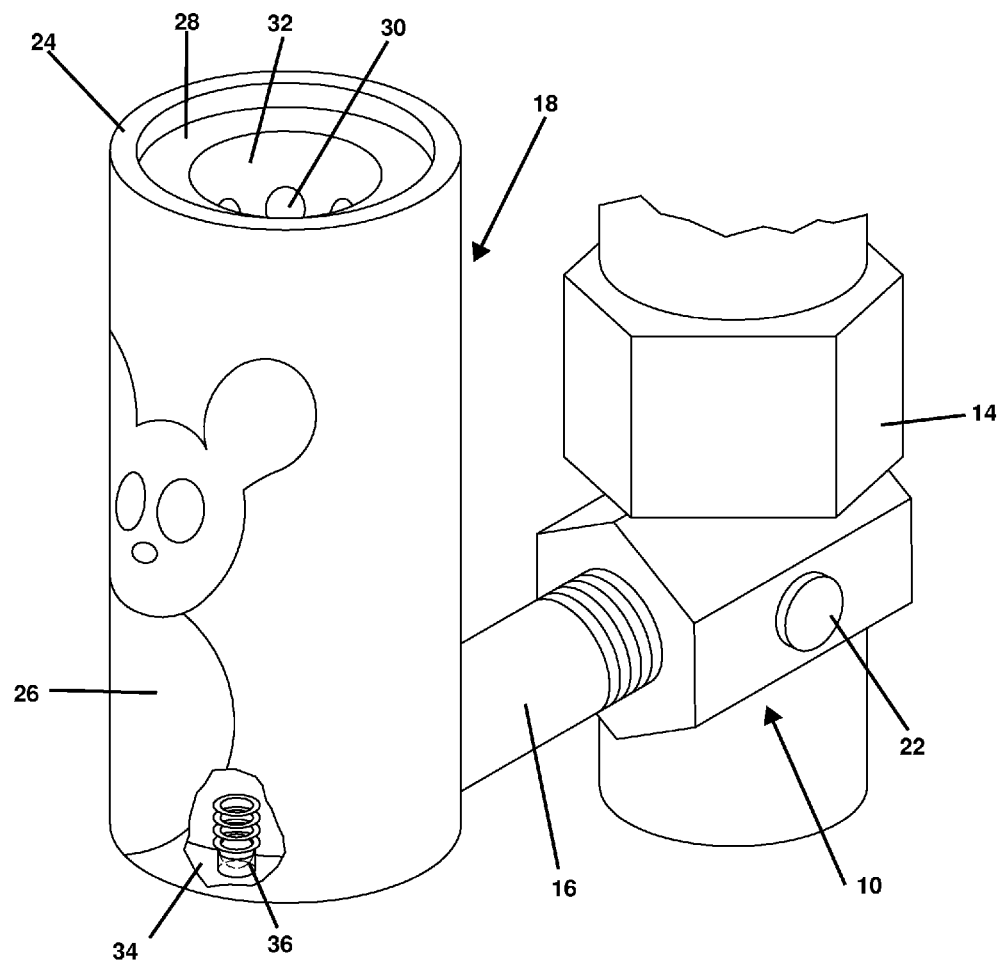
FIG. 3 shows a partially cut-away perspective view of the device for cleaning a toothbrush of FIG. 1, according to an embodiment of the disclosed technology.

Reference is now made to FIG. 3, which shows a partially cut-away perspective view of the device 10, showing a mechanism for draining water from cylindrical cleaning element 18. As seen, cylindrical cleaning element 18 includes a spring loaded release mechanism, including a port 34 driven by a spring 36 for releasing water from cylindrical cleaning element 18 after water has stopped flowing through the cleaning element 18. In some embodiments, the spring loaded release mechanism opens the port 34 when pressure within the pipe 16 and/or within cleaning element 18, such as when the faucet is closed and/or when valve or button 22 is switched from the cleaning position to the water-flow position.

Figure 4:
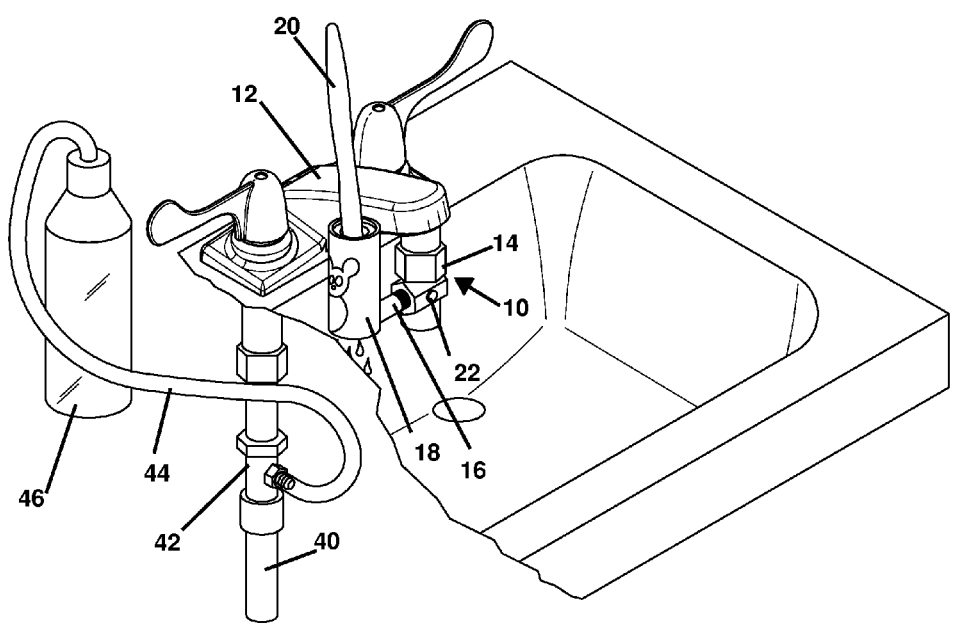
FIG. 4 shows a partially cut-away perspective view of the device for cleaning a toothbrush of FIG. 1, including a component for adding detergent to the water flowing through the device.

Reference is now made to FIG. 4, which shows a partially cut-away perspective view of the device 10 including an additional component for adding detergent to the water flowing through the device. As seen, a supply line 40 supplying water to faucet 12 has connected thereto, via a Venturi fitting 42 and one or more suitable pipes 44, a detergent receptacle 46 containing detergent suitable for cleaning a toothbrush, such as a non-toxic soap, disinfectant, or the like. The Venturi fitting 42 may be attached to the hot water supply line or to the cold water supply line, as desired and as is suitable for the detergent included in the receptacle 46.

When valve 22 is in the cleaning position, and pressure in device 10 is decreased, detergent is drawn from detergent receptacle 46 into supply line 40, via pipe 44 and Venturi fitting 42. The detergent is then mixed with water flowing through supply line 40 into faucet 12 and from there via pipe 16 into cleaning element 18, such that water jets expelled from nozzles 30 for cleaning the toothbrush 20 include the detergent and thus better clean and/or disinfect the toothbrush. When valve 22 switches to being in the water-flow position, the pressure in device 10 is increased, thus stopping the drawing of detergent from receptacle 46 into supply line 42 and from thence into cleaning element 18. The remainder of the detergent present in the pipe 44 or supply line 40 is expelled directly via the faucet 12 in the downward water flow direction, and once the remaining detergent has been expelled the faucet continues to expel water without the detergent.

Figure 5:
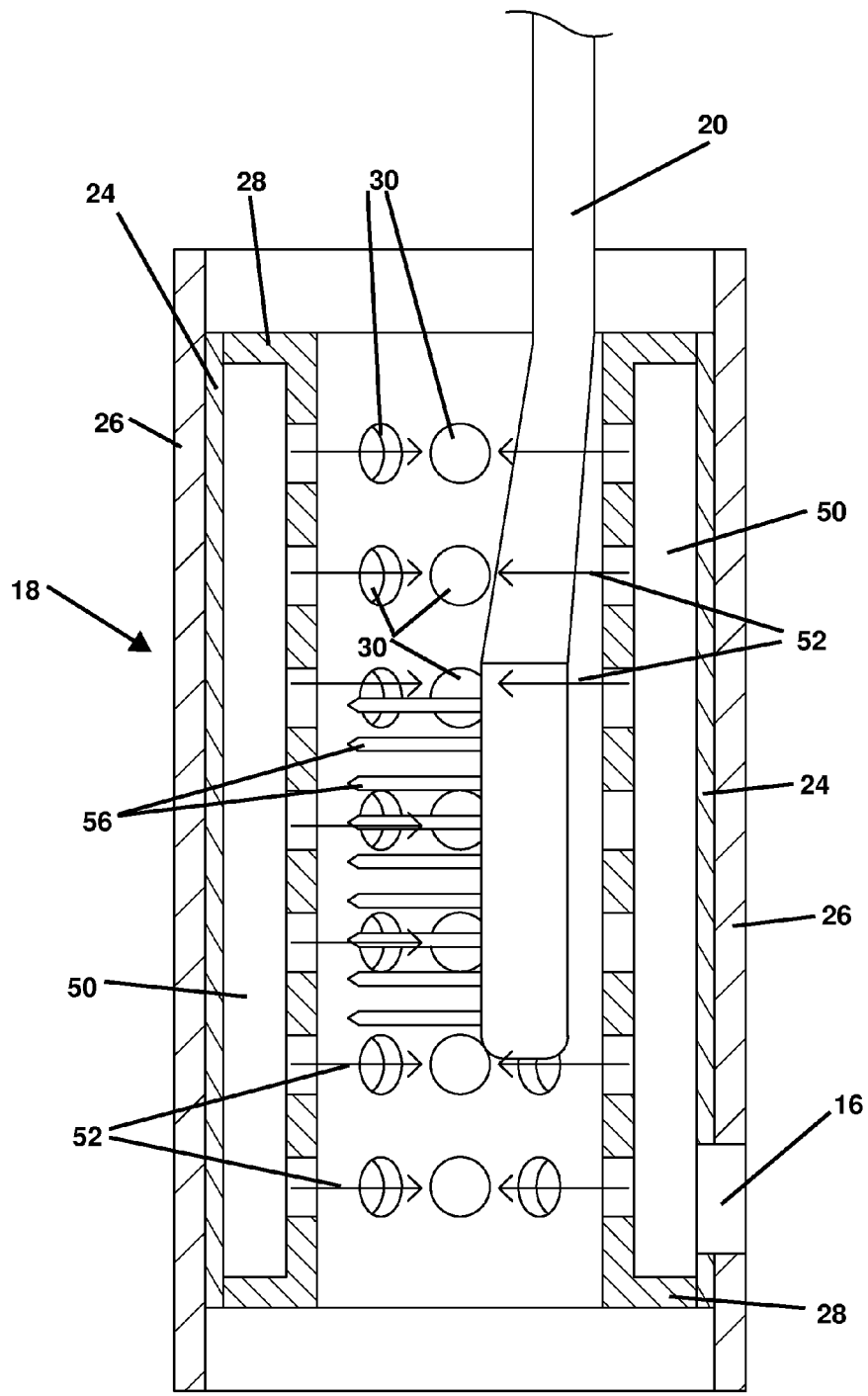
FIG. 5 shows a sectional view of a device for cleaning a toothbrush according to an embodiment of the disclosed technology, in use.

Reference is now made to FIG. 5, which shows a sectional view of device 10 for cleaning a toothbrush, and more specifically of cylindrical cleaning element 18, in use. As seen, a toothbrush is longitudinally disposed within cylindrical cleaning element 18, in the interior space 32. Water flows from pipe 16 into a space 50 defined between cylindrical housing 24 and water expelling cylindrical element 18, and from there is expelled, as water jets, from nozzles 30 disposed circumferentially on water expelling cylindrical element and/or insert 28, in the directions indicated by arrows 52.

A user cleaning toothbrush 20 moves the toothbrush longitudinally back and forth, or upwards and downwards, within cylindrical element 18 in the direction indicated by arrows 52, such that the water jets expelled by nozzles 30 impinge upon bristles 56 of toothbrush 20 and clean and/or disinfect the bristles. Since nozzles 30 are circumferentially disposed about cylindrical cleaning element 18, there is no significance to the direction in which the user places the toothbrush 20 within interior space 32, and the bristles 56 will be cleaned regardless of the direction they face.

While the disclosed technology has been taught with specific reference to the above embodiments, a person having ordinary skill in the art will recognize that changes can be made in form and detail without departing from the spirit and the scope of the disclosed technology. The described embodiments are to be considered in all respects only as illustrative and not restrictive. All changes that come within the meaning and range of equivalency of the claims are to be embraced within their scope. Combinations of any of the methods and apparatuses described hereinabove are also contemplated and within the scope of the invention.

The invention claimed is:

1. A method for cleaning a toothbrush, the method comprising:
   mounting an adapter on a faucet expelling water in a first direction, the adapter being in fluid flow communication with a cylindrical cleaning element disposed, when said adapter is mounted on said faucet, in a direction transverse to said first direction, said cylindrical cleaning element comprising multiple rows of circumferentially disposed nozzles for expelling water jets and having an interior space defined therein;
   activating said faucet such that when water is expelled from said faucet, at least some water is directed in said transverse direction and expelled through said nozzles; and
   moving a toothbrush to be cleaned longitudinally back and forth within said interior space such that said water jets impinge on bristles of said toothbrush for cleaning thereof.

2. The method of claim 1, wherein said mounting an adapter comprises mounting an adapter having a valve functionally associated therewith, said valve having a water-flow position in which water is expelled from said faucet in said first direction and a cleaning position in which all water flowing into said faucet is directed in said transverse direction and is expelled through said nozzles, said method further comprising, prior to said activating said faucet, moving said valve into said cleaning position.

3. The method of claim 2, further comprising, prior to said activating said faucet, fluidly connecting to a supply line of said faucet, via a Venturi fitting, a detergent receptacle, and wherein:
   said moving said valve into said cleaning position and said activating said faucet decreases pressure in said Venturi fitting such that detergent from said receptacle is drawn into said supply line and into nozzles.

4. The method of claim 1, further comprising, when a pressure changes in said adapter, opening a port in said cylindrical cleaning element and draining remaining water from said interior space of said cylindrical cleaning element.

5. The method of claim 4, further comprising turning off said faucet to cause said pressure change within said adapter.

6. The method of claim 4, further comprising moving said valve from said cleaning position to said water-flow position to cause said pressure change within said adapter.

7. The method of claim 1, further comprising placing a removable decorative outer sleeve about a cylindrical housing of said cylindrical cleaning element.

8. The method of claim 7, wherein said placing a removable decorative outer sleeve comprises placing a removable decorative outer sleeve which has printed thereon at least one of images and statements.

9. The method of claim 1, further comprising inserting a disposable insert inside said adapter before said step of activating such that portals in said disposable insert are aligned to said multiple rows of circumferentially disposed nozzles.

\* \* \* \* \*